United States Patent
Graumann

(10) Patent No.: US 8,788,039 B1
(45) Date of Patent: Jul. 22, 2014

(54) IMPLANTABLE CARDIAC STIMULATION DEVICE PROVIDING BICHAMBER AND MULTICHAMBER PACING TIMING AND METHOD

(75) Inventor: Robert J. Graumann, West Hartford, CT (US)

(73) Assignee: Pacesetter, Inc., Sylmar, CA (US)

( * ) Notice: Subject to any disclaimer, the term of this patent is extended or adjusted under 35 U.S.C. 154(b) by 1291 days.

(21) Appl. No.: 11/614,827

(22) Filed: Dec. 21, 2006

(51) Int. Cl.
*A61N 1/00* (2006.01)

(52) U.S. Cl.
USPC ............................................................ 607/9

(58) Field of Classification Search
USPC ............... 607/1, 2, 9, 14, 15, 17, 18, 19, 116, 607/119, 122, 123, 20, 21, 23, 24, 27, 28, 607/115
See application file for complete search history.

(56) References Cited

U.S. PATENT DOCUMENTS

| 5,466,254 | A | 11/1995 | Helland | |
|---|---|---|---|---|
| 6,324,425 | B1 * | 11/2001 | Blow et al. | 607/13 |
| 6,456,878 | B1 | 9/2002 | Yerich et al. | |
| 6,473,645 | B1 | 10/2002 | Levine | |
| 6,477,417 | B1 | 11/2002 | Levine | |
| 6,567,700 | B1 | 5/2003 | Turcott et al. | |
| 6,937,901 | B2 * | 8/2005 | Zhu et al. | 607/27 |
| 7,546,161 | B1 * | 6/2009 | Bjorling et al. | 607/28 |
| 2003/0004548 | A1 | 1/2003 | Warkentin | |
| 2003/0204212 | A1 | 10/2003 | Burnes et al. | |
| 2005/0137631 | A1 * | 6/2005 | Yu et al. | 607/9 |

FOREIGN PATENT DOCUMENTS

| EP | 1199085 A2 | 4/2002 |
|---|---|---|
| EP | 1260246 A2 | 11/2002 |
| WO | WO 03/002196 A2 | 1/2003 |
| WO | WO 03/037427 A1 | 5/2003 |
| WO | WO 03/092804 A1 | 11/2003 |

* cited by examiner

*Primary Examiner* — Christopher D Koharski
*Assistant Examiner* — Elizabeth K So

(57) ABSTRACT

An implantable cardiac stimulation device provides bichamber pacing. In accordance with a first embodiment, the device varies the interchamber pacing delay responsive to either sensed intrinsic activity or sensor measured activity of the patient. In another embodiment, the device times separate and independent AV intervals for providing pacing pulses to the right and left chambers.

10 Claims, 4 Drawing Sheets

IMPLANTABLE CARDIAC STIMULATION DEVICE PROVIDING BICHAMBER AND MULTICHAMBER PACING TIMING AND METHOD

FIELD OF THE INVENTION

The present invention generally relates to an implantable cardiac stimulation device that provides electrical therapy to a patient's heart. The present invention more particularly relates to such a device that provides bichamber and multichamber pacing therapy with improved pacing timing.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered to be comprised of two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing and/or sensing electrode configurations. In the unipolar configuration, the pacing stimulation pulses are applied or intrinsic responses are sensed between a single electrode carried by the lead, in electrical contact with the desired heart chamber, and the pulse generator case. The electrode serves as the cathode (negative pole) and the case serves as the anode (positive pole). In the bipolar configuration, the pacing stimulation pulses are applied or intrinsic responses are sensed between a pair of closely spaced electrodes carried by the lead, in electrical contact with the desired heart chamber, with the most proximal electrode serving as the anode and the most distal electrode serving as the cathode.

Pacemakers deliver pacing pulses to the heart to induce a depolarization and a mechanical contraction of that chamber when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm and optimize the hemodynamics of the heart.

Pacemakers are described as single-chamber or dual-chamber systems. A single-chamber system stimulates and senses in one chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode. Dual chamber represents coordinated atrial and ventricular activity, with the atrial contraction occurring at the appropriate amount of time before the ventricular contraction.

Recently, there has been the introduction of pacing systems that stimulate in corresponding chambers of the heart as, for example, the right ventricle (RV) and left ventricle (LV). These are termed biventricular stimulation devices and may be programmed to operate in single, dual or tri chamber modes. Future designs may include the left atrium (LA) and operate in quad chamber modes.

Biventricular pacing has been shown to coordinate contractions of the left and right ventricles, reduce the amount of blood flow that leaks through the mitral valve, and decreases the motion of the septal wall that separates the chambers of the heart. Such motion can affect the quantity of blood that the ventricle can pump out in a single beat. Biventricular pacing has its greatest benefit when optimally timed after the atrial contraction, and the right ventricular and left ventricular contractions are also optimally timed.

Biventricular pacing has been found to be particularly advantageous in patient's suffering from congestive heart disease because of the improved ability of the left ventricle to fully pump blood from the heart. As a result, patients are able to tolerate greater exertion, have a longer life span, and experience a higher quality of life.

The objective of any pacing system is to reproduce the normal conduction timing patterns and mechanical contractions of cardiac tissue in patients whose conduction system and/or myocardial substrate is diseased and does not function within normal limits. It is known in the normal heart that the timing cycles between chambers of the heart become shorter as the heart rate becomes faster. The need for pacing systems to provide rate responsive timing as the normal heart would, which adjusts timing cycles according to the heart rate, and cardiac resynchronization therapy (CRT) has been shown.

The term "rate responsive" refers to the adjustment of various timing cycles in the device, based upon the heart rate. The heart rate may be the intrinsic sinus rate, the ventricular rate, or a pacemaker driven rate determined by the activity sensor. When the patient becomes more active, the sensor detects the motion, and if natural mechanisms do not increase the heart rate accordingly, the pacemaker will do so. Rate responsiveness has been extended to multiple parameters. These parameters include, for example, AV delay, post ventricular atrial refractory period, and other refractory periods.

In today's dual chamber atrio-ventricular pacing systems, AV delays may be programmed to shorten as rates become faster, reproducing the response of the normal, healthy heart. Biventricular pacing systems, provide cardiac resynchronization therapy (CRT) by pacing the LV and RV either simultaneously or with a fixed offset, synchronized with the atria in order to improve cardiac output and oxygen uptake. This offset, referred to as the interventricular pacing delay (IVPD), allows the clinician to program one of the two ventricles to be paced first, with the other to follow at programmable IVP Delay.

Based on the other rate responsive timing changes in both the healthy heart and their device counterparts in pacing systems, it may be beneficial for interchamber pacing delays to be adjusted accordingly in order to maintain expected cardiac output and oxygen uptake at different rates. The present invention addresses that need.

SUMMARY OF THE INVENTION

The invention provides an implantable cardiac stimulation device comprising an activity sensor that senses activity of a patient and a pulse generator that provides a first pacing pulse to a first chamber of a heart and a second pacing pulse to a second chamber of the heart. The first and second chambers are corresponding chambers and the first and second pacing pulses are separated in time by an interchamber pacing delay. The device further comprises a timer that times the interchamber pacing delay. The interchamber pacing delay may be related to the activity of the patient sensed by the activity sensor.

The first and second chambers may be right and left ventricles, respectively, or left and right ventricles, respectively, of the heart and the interchamber pacing delay may be an interventricular pacing delay. The first and second chambers may be right and left atria, respectively, or left and right atria, respectively, of the heart.

A timer may determine a pacing rate responsive to the sensed patient activity. The timer may be responsive to the pacing rate and the interchamber pacing delay may in turn be related to the pacing rate. The pacing rate may be an atrial pacing rate.

The timer may begin timing the interventricular pacing delay responsive to delivery of the first pacing pulse. The pulse generator may deliver the first pacing pulse an AV interval after an atrial activation of the heart. The atrial activation may be a right atrial activation. Alternatively, the atrial activation may be a left atrial activation.

The interventricular pacing delay may be decreased with increased pacing rate. Alternatively, the interventricular pacing delay may be increased with increased pacing rate.

The invention further provides a method for use in an implantable cardiac stimulation device. The method comprises sensing activity of a patient, determining an interchamber pacing delay responsive to the sensed patient activity, and providing a first pacing pulse to a first chamber of the patient's heart. The method further comprises timing the interchamber pacing delay and providing a second pacing pulse to a second chamber of the patient's heart after timing the interchamber pacing delay, the first and second chambers being corresponding chambers.

The invention further provides an implantable cardiac stimulation device comprising a pulse generator that delivers pacing pulses to corresponding first and second chambers of a heart of a patient. The device further comprises timer that times first and second delay intervals from an activation of at least a third chamber of the heart to a time of delivery of pacing pulses to the first and second chambers respectively, the first and second delay intervals having durations which are independent from each other.

One of the delay intervals may be a fixed duration interval. The timer may vary the duration of one of the delay intervals responsive to a physiologic condition of the patient.

The device may further comprise an activity sensor that senses activity of the patient. The physiologic condition may be patient activity.

The first and second chambers may be a right ventricle and left ventricle respectively. The at least a third chamber may be a right or left atrium of the heart. The timer may be an AV interval timer and the first and second delay intervals may be first and second AV delay intervals.

The first and second chambers may be a right ventricle and left ventricle respectively. The timer may be an AV interval timer that times the first delay interval from activations of a right atrium of the heart to a time of delivery of pacing pulses to the right ventricle and times the second delay interval from activations of a left atrium of the heart to a time of delivery of pacing pulses to the left ventricle. The first and second delay intervals are first and second AV delay intervals. The timer may further time an interventricular delay from activations of the right atrium to when a pacing pulse is delivered to the left atrium. The second delay interval may then be timed from the left atrial pacing pulse.

The invention further provides a method for use in an implantable cardiac stimulation device. The method comprises timing first and second delay intervals from activations of at least a third chamber of a heart of a patient to a time of delivery of pacing pulses to first and second chambers of the heart respectively. The first and second delay intervals have durations independent from each other. The method further comprises delivering pacing pulses to the first and second chambers upon completion of the durations of the first and second delay intervals, respectively.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description includes the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
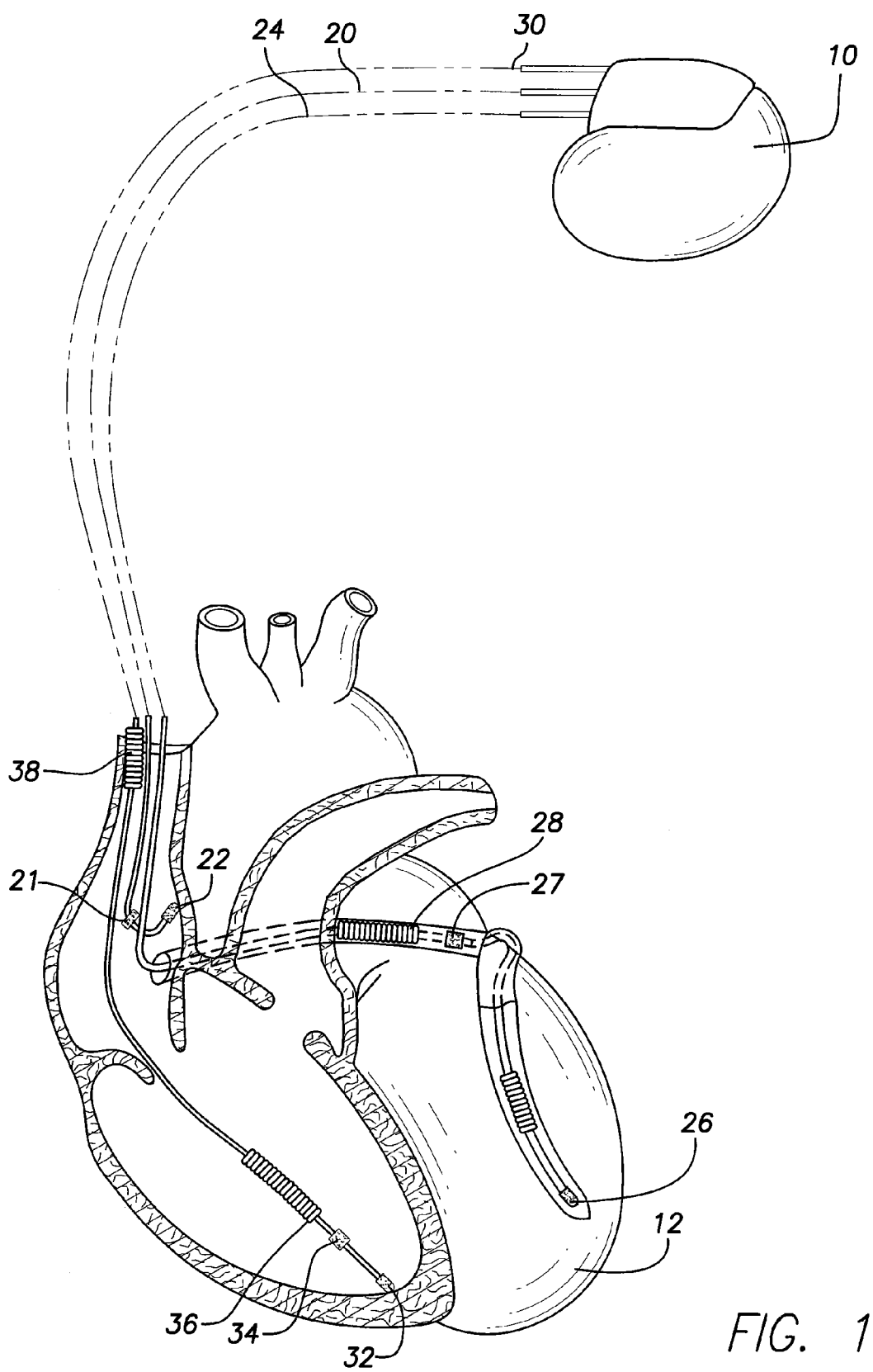
FIG. 1 is a simplified diagram illustrating an implantable stimulation device according to an embodiment of the present invention having at least three leads implanted into a patient's heart for delivering multi-chamber stimulation and shock therapy.

As shown in FIG. 1, there is a stimulation device 10 according to this embodiment of the present invention in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The lead 20 may include an optional ring electrode 21 which may be employed for pacing the right atrium with a bipolar electrode configuration including the ring electrode 21 and the tip electrode 22.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/ or small cardiac vein or any other cardiac vein accessible by the coronary sinus. Other embodiments would include epicardial leads placed in similar regions.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least one left atrial electrode 27, and shocking therapy using at least a left atrial coil electrode 28. For a complete description of a coronary sinus lead, see U.S. patent application Ser. No. 09/457,277, filed Dec. 8, 1999, entitled "A Self-Anchoring, Steerable Coronary Sinus Lead" (Pianca et. al); and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle. Alternative options are to place epicardial electrodes on multiple chambers, in specific locations.

Figure 2:
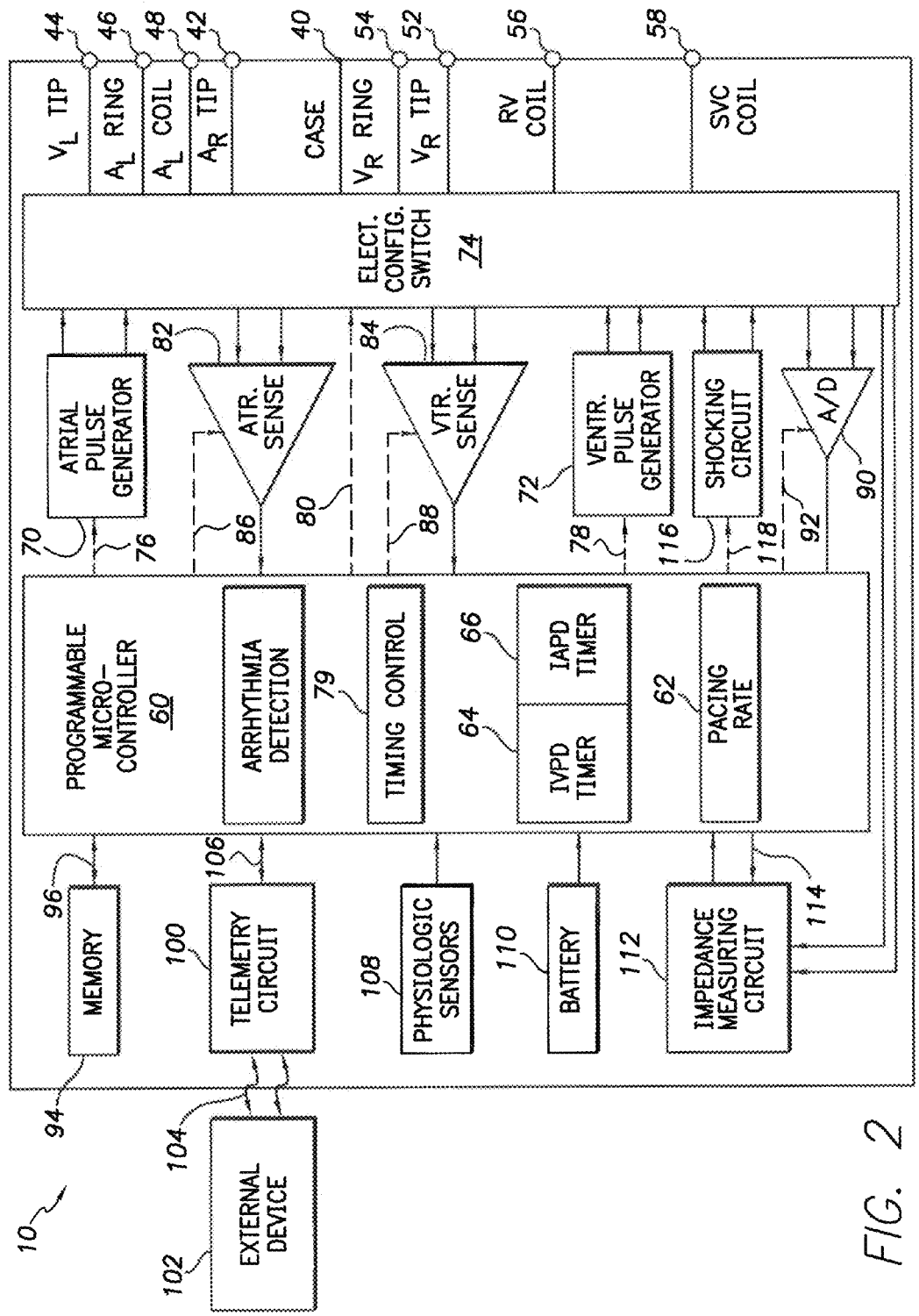
FIG. 2 is a functional block diagram of the multi-chamber implantable stimulation device of FIG. 1 illustrating the basic elements of a stimulation device which can provide cardioversion, defibrillation and pacing stimulation in four chambers of the heart including biventricular pacing therapy according to this embodiment.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. As will be seen subsequently, the timing control 79 finds particular use in accordance with this embodiment for timing AV delay intervals associated with the delivery of pacing pulses to the right ventricle and left ventricle during biventricular pacing.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to sense the physical activity or exercise state of the patient. The output of the physiological sensor 108 may be used to detect changes in cardiac output, changes in the physiological condition of the heart, or diurnal changes in activity (e.g., detecting sleep and wake states). The output of the physiological sensor may also be used, in accordance with this embodiment, by a pacing rate control 62 which responds to the output of sensor 108 to adjust various pacing parameters such as the rate, at which the atrial and ventricular pulse generators, 70 and 72, generate stimulation pulses. The intrinsic atrial rate to be tracked by the other chambers may also be used to adjust these pacing parameters because the intrinsic atrial rate would also be indicative of patient activity.

The intrinsic atrial rate or the sensor 108 indicated pacing rate may then be used to adjust the interventricular pacing delay (IVPD) as will be described subsequently in accordance with this embodiment. The intrinsic atrial rate or sensor 108 indicated pacing rate may further or alternatively be used by the timing control 79 to adjust one or more of the AV delay intervals associated with the delivery of pacing pulses to the right and left ventricles during biventricular pacing.

While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the activity level or exercise state of the patient.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries.

As further shown in FIG. 2, the device 10 is shown as having an impedance measuring circuit 112 which is enabled by the microcontroller 60 via a control signal 114. The impedance measuring circuit 112 may be able to measure such parameters as transthoracic impedance, which can represent respiration rate and thus activity level.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

During bichamber pacing, after one chamber receives a first pacing pulse, a second pacing pulse is delivered to another and corresponding chamber. In this manner, each of the right and left corresponding chambers receives a pacing pulse.

In accordance with one embodiment, during biventricular pacing, the further ventricular pacing pulse is delivered by the pulse generator 72 an interventricular pacing delay after the first ventricular pacing pulse is delivered. Similarly, during biatrial pacing, the further atrial pacing pulse is delivered by pulse generator 70 an interatrial pacing delay after the first atrial pacing pulse is delivered.

In accordance with another embodiment, separate, but independent, AV delay intervals are timed for delivery of a pacing pulse to each ventricle. Hence, since the durations of those AV delay intervals are independent, the delivery of the pacing pulses to the right and left ventricles will most likely occur at different times.

With respect to the first mentioned embodiment, the duration of the interventricular pacing delay is varied in response to the activity level of the patient as sensed by sensor 108 and, more particular, to the activity level adjusted rate determined by the pacing rate control 62. To this end, the device 10 is seen to further include an interchamber pacing delay timer 61 including an interventricular pacing delay (IVPD) timer 64 and an interatrial pacing delay (IAPD) timer 66. The IVPD timer 64 times the IVPD with a duration dependent on the pacing rate determined by the pacing rate control 62. The interatrial pacing delay (IAPD) timer 66 times interatrial pacing delays in a similar manner which may also be rate dependent. The pacing rate may be, for example, the atrial driven rate. It may alternatively be the paced ventricular rate.

The IVPD, for example, may be adjusted in accordance with the algorithm below.

$$RRIVPD = BIVPD - [(PR-BR) \times slope]$$

Where:
RRIVPD is the rate responsive interventricular pacing delay;
BIVPD is a baseline IVPD;
PR is the rate responsive pacing rate;
BR is a baseline rate; and
Slope is a scaling factor.

As an example, the BIVPD may be 10 (ten) milliseconds at a baseline (BR) of 90 beats per minute (bpm). The scaling factor (slope) may be chosen to be slow (0.1 for example), medium (0.2 for example), or fast (0.3 for example). Hence, if the medium slope of 0.2 is selected by programming, the RRIVPD at a rate of 120 bpm would be $$10 \text{ ms} - [(120 \text{ bpm} - 90 \text{ bpm}) \times 0.2] = 10 \text{ ms} - (30 \times 0.2)$$
$$\text{ms} = 10 \text{ ms} - 6 \text{ ms} = 4 \text{ ms}$$

Hence, the rate responsive IVPD would be 4 milliseconds and the second ventricular pacing pulse is delivered 4 ms after the first ventricular pacing pulse is delivered. The first ventricular pacing pulse may most often be delivered to the right ventricle followed by the second pacing pulse being delivered to the left ventricle. For some patients, however, It may be desirable to customarily deliver the first pacing pulse to the left ventricle. As will be seen from the algorithm, the first pacing may be delivered to the one ventricle at most pacing rates but that at some pacing rates, the RRIVD could be negative causing the first pacing pulse to now be delivered to the other ventricle and reverse the sequence.

The first pacing pulse may be timed from an activation of either one of the right or left atria. Upon an activation of the selected atrium, an AV interval is begun. The atrial activation that commences the timing of the AV interval may be a paced (A wave) or an intrinsic (P wave) event. At the end of the AV interval, if the ventricle to receive the first ventricular pacing pulse has not spontaneously depolarized, the first pacing pulse is delivered and timing of the RRIVPD is begun. The RRIVPD may be determined on a beat-by-beat basis as may be appreciated by those skilled in the art.

The scaling factor (slope) determines the rate of change of the RRIVPD with pacing rate. The rate of change may be programmably selected to be slow, medium, or fast as previously described. The slope or scaling factor may further be negative so that the IVPD decreases with increasing pacing rate.

Figure 3:
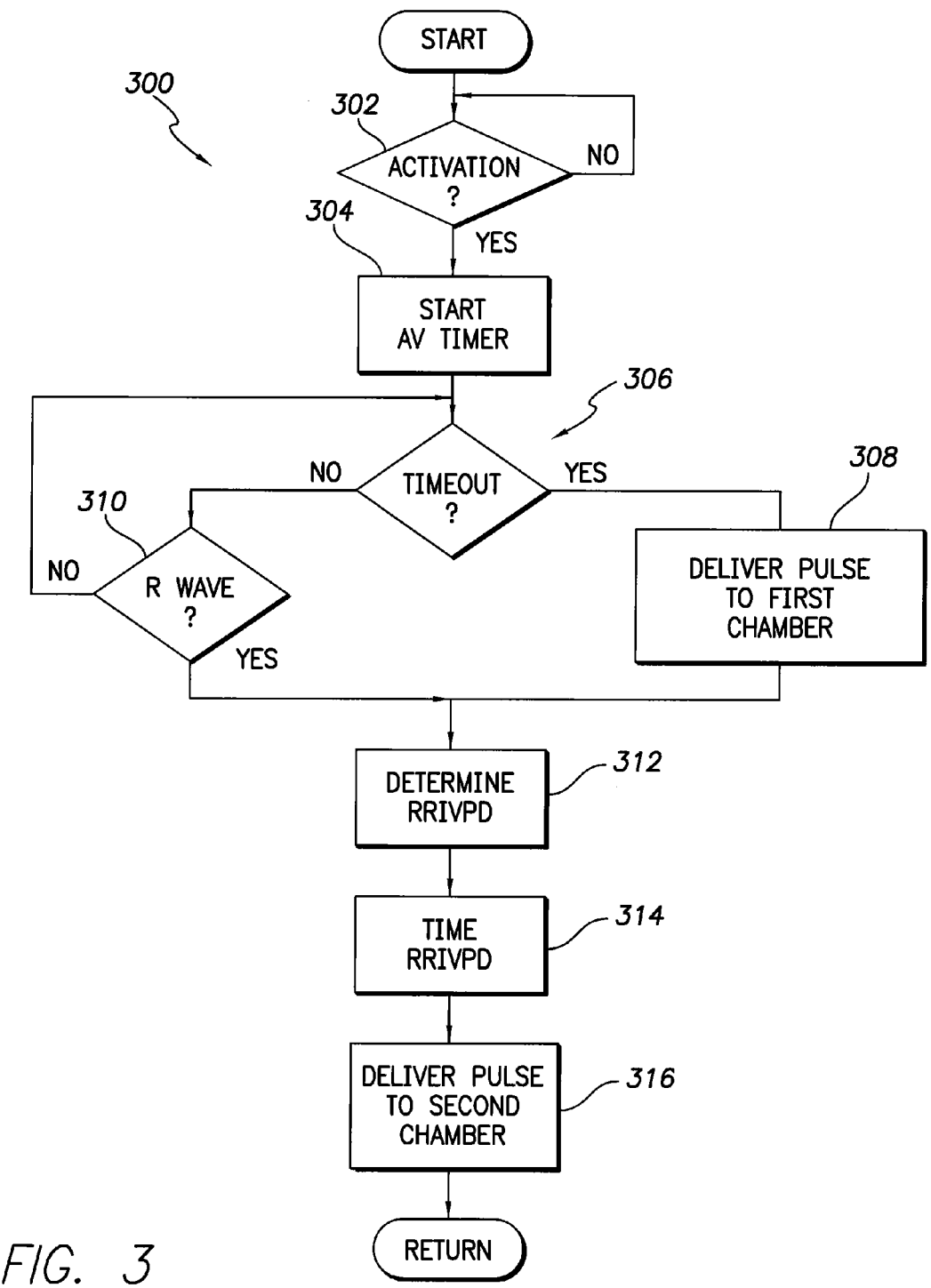
FIG. 3 is a flow chart describing an overview of the operation of one embodiment of the present invention.

The flow chart of FIG. 3 illustrates a process in accordance with this embodiment of the present invention. In this flow chart, and the flow chart of FIG. 4 described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process 300 of FIG. 3 initiates with decision block 302. Here it is determined if an activation (intrinsic or paced) has occurred in, for example, the right atrium. If not, the process continues to detect for such an activation. However, when an activation occurs, the process advances to activity block 304 where an AV timer is started to time an AV interval.

The process then proceeds to decision block 306 to determine if the AV interval has timed out. If the AV interval has timed out, the process proceeds to activity block 308 to deliver a pacing pulse to a first one of corresponding chambers, such as the right ventricle. If, in decision block 306 the AV interval has not timed out, and to support demand pacing, the process advances to decision block 310 to determine if an intrinsic activation (R wave) of the right ventricle has occurred. If not, the process returns to decision block 306. However, if an R wave does occur before the AV interval times out, the pacing pulse to the right ventricle is inhibited.

Upon an activation of the right ventricle, intrinsic or paced, the process advances to activity block 312 where the rate responsive interventricular pacing delay is determined. As previously described, the RRIVPD may be determined from the activity of the patient as determined by the physiologic sensor 108 (FIG. 2) or the pacing rate, for example. Once the RRIVPD is determined, the process immediately advances to activity block 314 where the determined RRIVPD is timed. When the timing of the RRIVPD is completed, a pacing pulse is delivered to the second chamber of the corresponding chambers, here, the left ventricle, in accordance with activity block 316. The process 300 then returns.

In accordance with the second embodiment, each of the right and left ventricles are paced after the completion of separate and independent AV delay intervals. The timing of both AV delay intervals may be commenced responsive to an activation (sensed or paced) of one of the atria, for example, the right atrium or the left atrium. Alternatively, and depending on the needs of a patient, the timing of the AV delay interval that determines the pacing time of one ventricle may be commenced responsive to an activation of one atria and the timing of the AV interval that determines the pacing time of the other ventricle may be commenced responsive to an activation of the other atria. Hence, for example, the delivery of pacing pulses to the right ventricle may be timed from activations of the right atrium while the delivery of pacing pulses to the left ventricle may be timed from activation of the left atrium. As previously mentioned, the independent AV delay intervals may be timed by the timing control 79.

Still further, the timer 66 may time an interatrial pacing delay from the right atrial activation to when a left atrial pacing pulse is to be delivered. The first AV delay interval may be timed from the right atrial activation and the second AV delay interval may be timed from the left atrial pacing pulse.

Either one or both of the AV delay intervals may have a fixed duration or a duration which varies with changes in a sensed physiologic condition of the patient. The sensed physiologic condition may be activity level as sensed by the physiologic sensor 108 or a hear rate as determined by the pacing rate control 62 and which may be related to sensed patient activity.

If pacing rate is used to vary the AV delay interval associated with one of the ventricles, the following algorithm may be employed.

$$RRAVI = BAVI - [(PR-BR) \times slope]$$

Where:
RRAVI is the rate responsive AV delay interval;
BAVI is a baseline AV delay interval at a base rate BR;
PR is the present pacing rate; and
Slope is the rate of change in the BAVI.

As an example, the baseline AV delay interval may be 150 ms, the baseline rate may be 90 bpm, and the slope may be 1 ms for each bpm change in pacing rate. Hence, if the present pacing rate is 130 bpm, the corresponding RRAVI would be $$150 - [(130-90) \times 1] = 110 \text{ ms}$$

The slope may, as in the previous embodiment, be selectable. It may be one of fast (3), medium (2), slow (1), and very slow (0.5) for example. The very slow slope allows finer adjustment.

The AV delay interval to timeout first determines which ventricle receives the first ventricular pacing pulse. When the ventricles are paced in a demand mode, if the AV delay interval should fail to timeout because of a sensed intervening intrinsic depolarization, both the first and second ventricular pacing pulses may be inhibited. However, if the first ventricular pacing pulse is delivered, the second pacing pulse may be delivered upon timeout of its AV delay interval regardless of intrinsic activity of that chamber.

Figure 4:
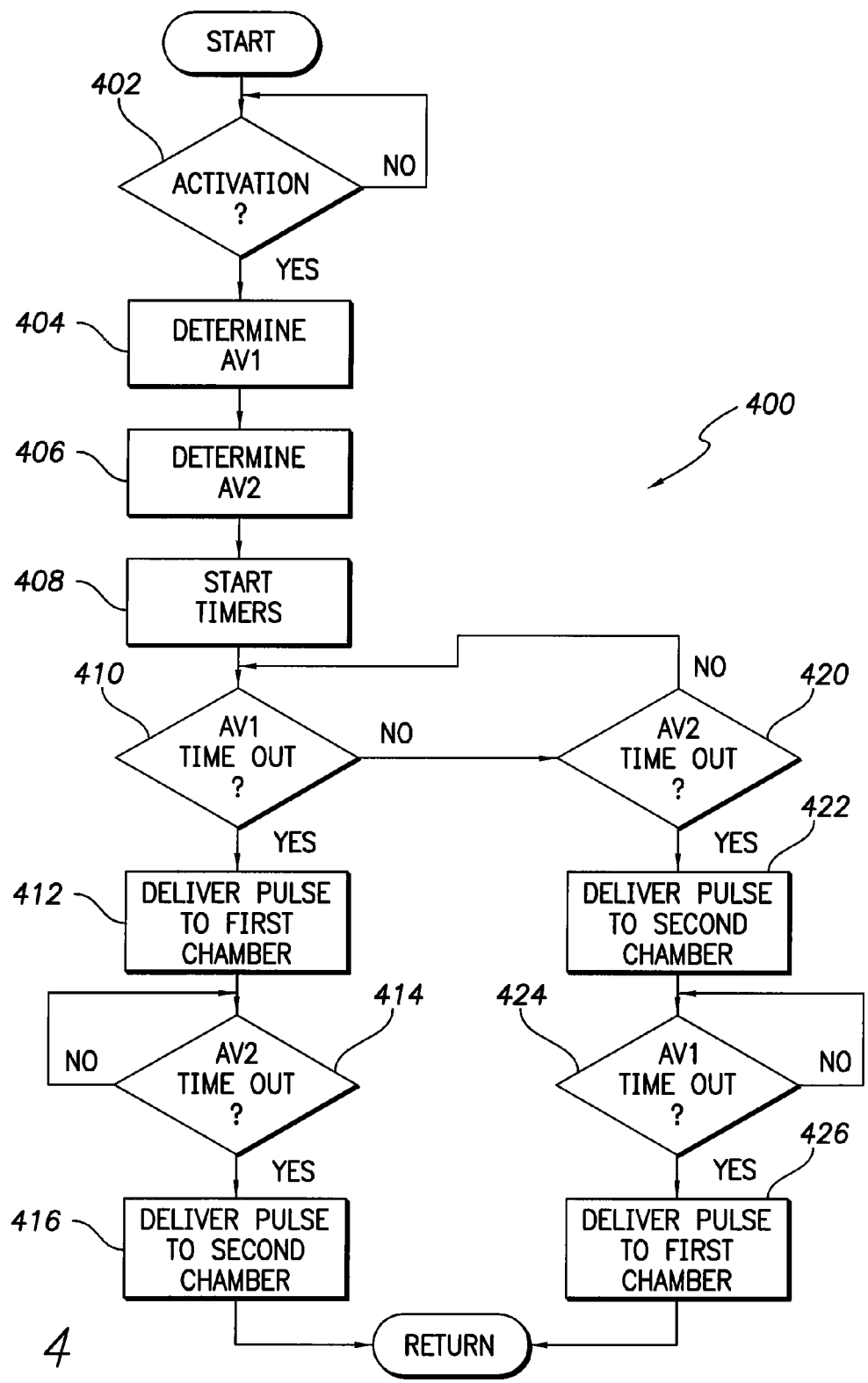
FIG. 4 is a flow chart describing an overview of the operation of another embodiment of the present invention.

The flow chart of FIG. 4 illustrates a process in accordance with this further embodiment of the present invention. The process 400 of FIG. 4 initiates with decision block 402. Here it is determined if an activation (intrinsic or paced) has occurred in, for example, the right atrium. If not, the process continues to detect for such an activation. However, when an activation occurs, the process advances to successive activity blocks 404 and 406 where a first AV interval and a second AV interval, respectively, are determined. The first AV interval may be, for example, the time from the activation determined in decision block 402 to when a first one of corresponding chambers, for example, the right ventricle, is to be paced absent an intrinsic activation of the right ventricle prior to the time out of the first AV interval. Similarly, the second AV interval may be, for example, the time from the activation determined in decision block 402 to when a second one of corresponding chambers, for example, the left ventricle, is to be paced absent an intrinsic activation of the left ventricle prior to the time out of the second AV interval. The first and second AV intervals may be determined independently from one another and relate to the activity level of the patient as determined by the physiologic sensor 108 or the pacing rate. Once the first and second AV intervals are determined in accordance with activity blocks 404 and 406, counters are started to time the same in activity block 408.

Next, the process 400 advances to decision block 410 to determine if the first AV interval has timed out. If it has, the process advances to activity block 412 where a pacing pulse is delivered to the first chamber (right ventricle) of the corresponding chambers (ventricles). The process then advances to decision block 414 to determine if the second AV interval has timed out. If it has, the process proceeds to activity block 416 for the delivery of a pacing pulse to the second chamber (left ventricle) of the corresponding chambers (ventricles). The process then returns. If in decision block 414 the second AV interval has not yet timed, the process continues to detect for such a time out. Of course, as may be appreciated, either pacing pulse may be inhibited if an R wave should occur prior to time out of its associated AV interval without departing from the present invention. In that case, the intrinsic event would take the place of the pacing pulse delivery.

If in decision block 410 it is determined that the first AV interval has not timed out, the process advances to decision block 420 to determine if the second AV interval has timed out. If it has not, the process returns to decision block 410. If it has however, the process advances to activity block 422 where a pacing pulse is delivered to the second chamber (left ventricle) of the corresponding chambers (ventricles). The process then advances to decision block 424 to determine if the first AV interval has timed out. If the AV interval has timed out, the process proceeds to activity block 426 for the delivery of a pacing pulse to the first chamber (right ventricle) of the corresponding chambers (ventricles). The process then returns. If in decision block 424 the first AV interval has not yet timed out, the process continues to detect for such a time out. Again, as may be appreciated, either pacing pulse may be inhibited if an R wave should occur prior to time out of its associated AV interval without departing from the present invention. In that case, the intrinsic event would take the place of the pacing pulse delivery.

The present invention, as may be seen from the various embodiments disclosed herein, allows great flexibility in determining when the ventricles should be paced in biventricular pacing. Pacing times and sequence may be independently implemented to suit the particular needs of a patient. In addition, timing of pacing pulse delivery may be automatically varied to suit the hemodynamic demands of the patient.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device comprising:
    an activity sensor that senses an activity level of a patient, wherein the activity level of the patient corresponds to an exercise state of the patient;
    a pulse generator that provides a first pacing pulse to a first chamber of a heart and a second pacing pulse to a second chamber of the heart, the first and second chambers being corresponding chambers and the first and second pacing pulses being separated in time by an interchamber pacing delay; and
    a timer that times the interchamber pacing delay, the interchamber pacing delay being related to the activity level of the patient sensed by the activity sensor, wherein the first and second chambers are a right ventricle and left ventricle respectively of the heart and wherein the interchamber pacing delay is an interventricular pacing delay, and wherein the timer automatically adjusts the interchamber pacing delay based on changes in the patient activity level.

2. The device of claim 1 further comprising a timing control that determines a pacing rate responsive to the sensed patient activity, and wherein the timer is responsive to the pacing rate and the interchamber pacing delay is related to the pacing rate.

3. The device of claim 2 wherein the pacing rate is an atrial pacing rate.

4. The device of claim 2 wherein the timer begins timing the interventricular pacing delay responsive to delivery of the first pacing pulse.

5. The device of claim 2 wherein the pulse generator delivers the first pacing pulse an AV interval after an atrial activation of the heart.

6. The device of claim 5 wherein the atrial activation is a right atrial activation.

7. The device of claim 5 wherein the atrial activation is a left atrial activation.

8. The device of claim 2 wherein the interventricular pacing delay is decreased with increased pacing rate.

9. The device of claim 2 wherein the interventricular pacing delay is increased with increased pacing rate.

10. An implantable cardiac stimulation device comprising:
    an activity sensor that senses an activity level of a patient, wherein the activity level of the patient corresponds to an exercise state of the patient;
    a timing control that determines a pacing rate responsive to the sensed patient activity level;
    a pulse generator that provides a first pacing pulse to a first chamber of a heart and a second pacing pulse to a second chamber of the heart, the first and second chambers being corresponding chambers and the first and second pacing pulses being separated in time by an interchamber pacing delay; and
    a timer that times the interchamber pacing delay, the interchamber pacing delay being related to the pacing rate, wherein the corresponding chambers are ventricles of the heart and wherein the interchamber pacing delay is an interventricular pacing delay, and wherein the timer automatically adjusts the interchamber pacing delay based on changes in the patient activity level.

* * * * *